(12) United States Patent
Barge et al.

(10) Patent No.: US 12,188,895 B2
(45) Date of Patent: Jan. 7, 2025

(54) NANOPORE TRANSISTOR FOR BIOSENSING

(71) Applicant: IMEC VZW, Leuven (BE)

(72) Inventors: David Barge, Schaerbeek (BE); Bert Du Bois, Blanden (BE); Simone Severi, Leuven (BE); Ashesh Ray Chaudhuri, Heverlee (BE)

(73) Assignee: IMEC VZW, Leuven (BE)

( * ) Notice: Subject to any disclaimer, the term of this patent is extended or adjusted under 35 U.S.C. 154(b) by 386 days.

(21) Appl. No.: 17/692,717

(22) Filed: Mar. 11, 2022

(65) Prior Publication Data

US 2022/0334079 A1 Oct. 20, 2022

(30) Foreign Application Priority Data

Apr. 16, 2021 (EP) .................................... 21168769

(51) Int. Cl.
*H01L 21/00* (2006.01)
*G01N 27/414* (2006.01)

(52) U.S. Cl.
CPC ..... *G01N 27/4145* (2013.01); *G01N 27/4146* (2013.01)

(58) Field of Classification Search
CPC .................. G01N 27/4145; G01N 27/4146
See application file for complete search history.

(56) References Cited

U.S. PATENT DOCUMENTS

| 2007/0178507 A1* | 8/2007 | Wu .................. G01N 33/48721 |
| | | 435/7.1 |
| 2016/0116435 A1 | 4/2016 | Cheng et al. |
| 2019/0271660 A1 | 9/2019 | Chan et al. |

(Continued)

FOREIGN PATENT DOCUMENTS

| EP | 2 237 027 A1 | 10/2010 |
| EP | 3 502 688 A1 | 6/2019 |

(Continued)

OTHER PUBLICATIONS

Ren, R., et al., "Nanopore Extended Field-Effect Transistor for Selective Single-Molecule Biosensing", Nature Communications, 2017, vol. 8, Article No. 586, pp. 1-9.

(Continued)

*Primary Examiner* — Richard A Booth
(74) *Attorney, Agent, or Firm* — McDonnell Boehnen Hulbert & Berghoff LLP

(57) ABSTRACT

A method for forming a nanopore transistor and a nanopore transistor is provided. The method includes: (a) forming an aperture in a filler material by: (i) providing a fin comprising a semiconductor layer and a top layer; (ii) patterning the top layer to form a pillar; (iii) embedding the pillar in a filler material; (iv) removing the pillar, leaving an aperture; (v) lining the aperture with a spacer material; (b) forming a nanopore by etching through the aperture; (b) lining the nanopore with a dielectric, (c) forming a source and a drain by either: between steps a.ii and a.iii, doping the bottom semiconductor layer by using the pillar as a mask, or after step c, filling the aperture with a sealing material, thereby forming a post; removing the filler material; doping the bottom semiconductor layer by using the post as a mask; and removing the sealing material.

16 Claims, 8 Drawing Sheets

(56) References Cited

U.S. PATENT DOCUMENTS

2020/0072788 A1* 3/2020 Hellings ............... B82Y 15/00
2020/0141898 A1* 5/2020 Martens ............ G01N 27/4145
2021/0184053 A1* 6/2021 Chen ................. G01N 27/4146

FOREIGN PATENT DOCUMENTS

EP       3 536 660 A1    9/2019
WO    2008/132643 A1   11/2008

OTHER PUBLICATIONS

Extended European Search Report from the European Patent Office, mailing date Oct. 20, 2021, for European Patent No. 21168769.4, pp. 1-7.

* cited by examiner

NANOPORE TRANSISTOR FOR BIOSENSING

CROSS-REFERENCE

The present application claims priority from European Patent Application No. 21168769.4, filed on Apr. 16, 2021, which is incorporated by reference in its entirety.

TECHNICAL FIELD OF THE DISCLOSURE

The present disclosure relates to the field of biosensing, and more particularly to the field of nanopore transistors for sensing the presence of polynucleic acids such as deoxyribonucleic acid (DNA) or ribonucleic acid (RNA).

BACKGROUND OF THE DISCLOSURE

In some biopolymer sensing technologies (see e.g., Ren, R. et al., Nat. Commun. 8, 586 (2017)), long-chain biopolymers such as, e.g., DNA may be characterized by using a semiconductor device based on a field-effect transistor (FET), such as, e.g., a metal oxide semiconductor FET (MOSFET), comprising a drain region, a source region, a channel region, and an opening through the channel region allowing the biopolymer to pass. Such devices are now gaining credibility with respect to DNA sensing.

The voltage potential applied across the drain and source regions creates a gradient that causes the biopolymer to move through the opening. In case of a DNA or RNA strand, the sequence of bases may induce charges, which can form a conducting channel in the semiconductor channel region between the drain and source regions, resulting in a current variation that can be detected by, e.g., a current meter. Each different type of base A, C, G, and T (in case of a DNA strand) may induce a current having a particular magnitude and waveform representative of the respective type of bases. Thus, by studying the current variation as the sample passes through the opening, the sequence of bases can be detected.

Some of these technologies rely on an opening having a highly controlled size and shape. Depending on the type of biopolymer strand to be sensed, the opening is sometimes configured to have a diameter small enough to allow only one stand to pass through the opening at any given time. DNA sequencing, for example, may be performed using an opening having a width within a nanoscale range, such as within the range of about 1 nm to about 100 nm such as an opening having a diameter of 10 nm. Forming such small openings is technically challenging, especially in terms of alignment.

Typically, as mask to mask overlay meet values down to 10 nm (using 193 nm lithography), obtaining the desired position of a nanopore seems to be only feasible by defining the hole position on the same mask designing the active area of the nanowire. However, the state-of-the-art of the 193 nm lithography does not allow resolving the print of a narrow hole into a narrow nanowire. Progress in Deep UV lithography might finally make this doable but at a costly effort.

Efforts to find an alternative solution can be found, for instance, in US Patent Application Pub. No. 2019/0271660 where a method for forming a nanopore is described which comprises the steps of:
providing a fin structure comprising a bottom layer and a top layer;
patterning the top layer to form a pillar;
laterally embedding the pillar in a filler material;
forming an aperture in the filler material by removing the pillar; and
forming the nanopore in the bottom layer by etching through the aperture.

In this method, an etch mask (the pillar) is positioned by self-alignment in the lateral direction of the fin structure, thereby enabling the formation of a semiconductor structure having an opening or pore laterally centered in the fin structure. However, there is still room for improvement over this patent application with respect to the positioning of other elements of a nanopore transistor such as the channel, the source, and the drain. Considering the accuracy demanded to have an operational device, using a new mask to position source, drain, and channel associated with the transistor after the nanopore is created is not realistic.

There is therefore a need in the art for methods overcoming one or more of the problems described above.

SUMMARY OF THE DISCLOSURE

It is an object of the present disclosure to provide good nanopore transistors for biosensing as well as methods for producing the same.

The above objective is accomplished by a method and device according to the present disclosure.

Some embodiments of the present disclosure can enable a nanopore to be correctly formed on such a fin.

Some embodiments of the present disclosure can allow for an improved definition and positioning of the nanopore compared to etching the nanopore in a single lithographic step.

Some embodiments of the present disclosure can enable a nanopore to be correctly aligned on a fin having a width close to the width of the nanopore. In the multiple patterning process used in step a., the position of the nanopore can be aligned in a width direction, or lateral direction of the fin and aligned in a length direction of the fin.

Some embodiments of the present disclosure can enable the formation of a nanopore that is self-aligned in the lateral direction of the fin.

Some embodiments of the present disclosure can allow a particularly good lateral alignment of the nanopore, thereby allowing for a particularly high ratio between the nanopore width and the fin width. A reduced fin width, or a reduced cross-section of the fin, can be beneficial in that it may reduce the drive current during the operation of the device.

Some embodiments of the present disclosure can allow a nanopore and a transistor to be co-fabricated without additional lithography process, in such a way that associated source and drain regions around the nanopore are self-aligned.

Some embodiments of the present disclosure can allow for the size of the nanopore to be easily adapted to accommodate and/or target different biosensing applications without added patterning complexity.

Some embodiments of the present disclosure can allow the formation of nanopore transistors having a nanopore small enough to be used for sensing polymers such as, e.g., DNA or RNA strands. Embodiments of the present disclosure can be particularly beneficial for biosensing applications and especially for massive parallel biosensing applications such as DNA sequencing.

Some embodiments of the present disclosure can allow only a limited number of masks (typically two) to achieve an excellent positioning of a nanopore in the center for the transistor and channel width, and at equidistance of both the source and the drain by a self-aligning integration process.

Some embodiments of the present disclosure can use standard semiconductor manufacturing steps, thereby enabling the mass production of nanopore transistors at low cost.

Some embodiments of the present disclosure can be compatible with allowing fluidic access to the nanopore, thereby making the resulting devices compatible with sequencing applications.

In a first aspect, the present disclosure relates to method for forming a nanopore transistor for biosensing, comprising:
 a. Forming an aperture in a filler material by:
  i. providing a fin structure comprising at least a bottom semiconductor layer and a top layer;
  ii. patterning the top layer to form a pillar;
  iii. laterally embedding the pillar in a filler material;
  iv. forming an aperture in the filler material by removing the pillar;
  v. lining the aperture with a spacer material, thereby reducing a size of the aperture;
characterized in that the method further comprises:
 b. forming a nanopore in the bottom semiconductor layer by etching through the aperture;
 c. lining (S54) the nanopore (10) with a gate dielectric material (170), thereby forming a gate dielectric;
 d. Forming source and a drain by either:
  i. Between steps a.ii. and a.iii., doping the bottom semiconductor layer by ion implantation using the pillar as a mask, or
  ii. After step b., and usually after step c.,
   filling the aperture with a sealing material so that the sealing material is coplanar with the filler material, thereby forming a post comprising the sealing material and the spacer material;
   removing the filler material selectively with respect to the post, thereby exposing a part of the bottom semiconductor layer;
   doping the bottom semiconductor layer by ion implantation by using the post as a mask; and
   removing the sealing material.

Two main embodiments are therefore described in the first aspect. In the first main embodiment (depicted in FIG. 18), step d is performed after step b and usually after step c. Performing step d after step c can be beneficial because it allows having a high thermal budget for the formation of the gate dielectric without affecting the doping. In the second main embodiment (depicted in FIG. 19), step d is performed between step a.ii and step a.iii. This embodiment can be beneficial because it can require fewer steps than the first main embodiment. Both main embodiments share benefits of the present disclosure (correctly formed nanopore of adaptable size with good positioning on a fin, source and drain regions that are self-aligned with the nanopore, a limited number of masks, and a low-cost production).

In a second aspect, the present disclosure relates to a nanopore transistor or biosensing, formed by a method according to any one of the preceding claims.

In embodiments, the nanopore transistor for biosensing may comprise a fin structure comprising a semiconductor layer having:
 i. a top surface having two longitudinal parallel sides separated by a width W of from 20 to 40 nm,
 ii. a nanopore piercing the semiconductor layer and lined with a gate dielectric material, and
 iii. ion implantation in the semiconductor layer forming a source and a drain separated by a distance D of 20 to 60 nm, wherein the nanopore is centered with respect to the source and the drain so that the distance Ds along the top surface between the nanopore and the source can be within 3 nm of the distance Dd along the top surface between the nanopore and the drain.

In embodiments, the nanopore may be centered with respect to the width W so that the distances d1 and d2 between each longitudinal side and the nanopore can be within 3 nm of one another.

In embodiments, the ratio between a width of the nanopore, measured in the plane of the top surface of the fin and along the width W of the fin, and the width W of the top surface of the fin may range from 0.12 to 0.85.

Particular aspects of the disclosure are set out in the accompanying independent and dependent claims. Features from the dependent claims may be combined with features of the independent claims and with features of other dependent claims as appropriate and not merely as explicitly set out in the claims.

Although there has been constant improvement, change, and evolution of devices in this field, the present concepts are believed to represent substantial new and novel improvements, including departures from prior practices, resulting in the provision of more efficient, stable, and reliable devices of this nature.

The above and other characteristics, features, and benefits of the present disclosure will become apparent from the following detailed description, taken in conjunction with the accompanying drawings, which illustrate, by way of example, the principles of the disclosure. This description is given for the sake of example only, without limiting the scope of the disclosure. The reference figures quoted below refer to the attached drawings.

BRIEF DESCRIPTION OF THE DRAWINGS

FIG. 1 illustrates an exemplary structure (100) resulting from step a.i is depicted. In embodiments, step a.i may comprise forming the fin structure by a lithography comprising a dry etching step. The fin structure (100) comprises a bottom semiconductor layer (110) and a top layer (120). The width of the fin may for instance range from 20 to 40 nm but the present method is applicable to wider or narrower fins. In embodiments, the fin structure has a bottom semiconductor layer (110) having a top surface having two longitudinal parallel sides separated by a width of from 20 to 40 nm. A reduced fin width, or a reduced cross-section of the fin, can be beneficial in that it may reduce the drive current during the operation of the device.

FIG. 2 shows a line mask (150) intersecting the fin structure in an exemplary structure.

FIG. 3 where an exemplary structure resulting from step a.ii is depicted. This structure comprises a pillar (122) and may for instance be formed by self-aligning (S22) the pillar on the bottom layer using a line mask (150) intersecting the fin structure, as depicted in FIG. 2 for an exemplary embodiment.

FIG. 4 shows that step a.iii may include a first sub-step of embedding the pillar in the filler material in such a way that all the pillar surfaces are covered.

FIG. 5 shows a second sub-step of removing a top portion of the filler material so as to expose the top surface of the pillar.

FIG. 6 shows an exemplary structure resulting from step a.iv.

FIG. 7 shows an exemplary structure resulting from step a.v.

FIG. 8 shows an exemplary intermediate formed during step b is depicted. Step b of the method is performed after step a, usually directly after step a.

FIG. 9 shows an exemplary structure where the method further comprises a step c after step b, of lining (S54) the nanopore with a gate dielectric material (170), thereby forming a gate dielectric.

FIG. 10 shows an exemplary structure after step (S60) of filling the aperture during step d.ii including overfilling the aperture (140) with a sealing material (180) so that the sealing material (180) covers part of the filler material (130).

FIG. 11 shows an exemplary structure following the step of overfilling the aperture is followed by removing a top portion (181) of the sealing material (180) until it no longer covers any filler material.

FIG. 12 shows an exemplary structure following the step (S70) of removing the filler material in step d.ii for an exemplary embodiment of the present disclosure. The resulting structure has the bottom semiconductor layer exposed around the post.

FIG. 13 shows an exemplary structure following the doping step (S80) in step d.ii.

FIG. 15 shows an exemplary structure t after removing (S90, the sealing material (180).

Figure 1:
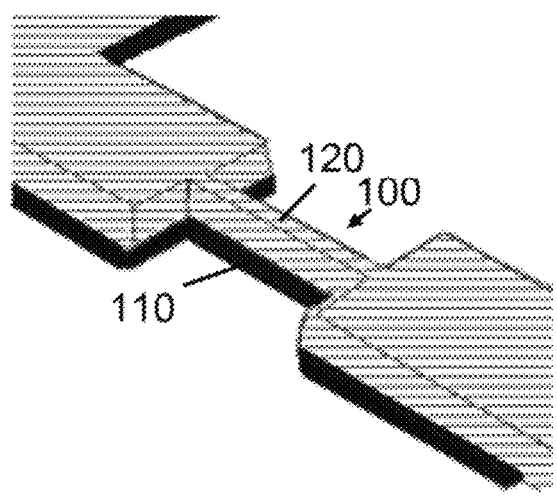
FIGS. 1 to 3 are schematic representations of perspective views of intermediate structures formed in steps a.i through a.ii of an embodiment of the present disclosure.

In the different figures, the same reference signs refer to the same or analogous elements.

DESCRIPTION OF ILLUSTRATIVE EMBODIMENTS

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the disclosure.

Furthermore, the terms "first," "second," "third," and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms "top," "bottom," "over," "under," and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps, or components as referred to, but does not preclude the presence or addition of one or more other features, integers, steps or components, or groups thereof. The term "comprising" therefore covers the situation where only the stated features are present (and can therefore always be replaced by "consisting of" in order to restrict the scope to said stated features) and the situation where these features and one or more other features are present. The word "comprising" according to the disclosure therefore also includes as one embodiment that no further components are present. Thus, the scope of the expression "a device comprising means A and B" should not be interpreted as being limited to devices consisting only of components A and B. It means that with respect to the present disclosure, the only relevant components of the device are A and B.

Reference throughout this specification to "one embodiment" or "an embodiment" means that a particular feature, structure, or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures, or characteristics may be combined in any suitable manner, as would be apparent to one of ordinary skill in the art from this disclosure, in one or more embodiments.

Similarly, it should be appreciated that in the description of exemplary embodiments of the disclosure, various features of the disclosure are sometimes grouped together in a single embodiment, figure, or description thereof for the purpose of streamlining the disclosure and aiding in the understanding of one or more of the various disclosed aspects. This method of disclosure, however, is not to be interpreted as reflecting an intention that the claimed disclosure requires more features than are expressly recited in each claim. Rather, as the following claims reflect, disclosed aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the disclosure.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

The following terms are provided solely to aid in the understanding of the disclosure.

As used herein, a "pillar" refers to a structure extending in the vertical direction, e.g., a direction normal to a major surface of the substrate. The pillar may also be referred to as a post, a dot, or mask feature that can be used as a sacrificial structure for forming the aperture through which the nanopore is etched.

As used herein, the term "vertical" (for instance with reference to a direction or a plane or the pillar) denotes a geometrical axis being parallel to a stacking direction of the layers of the fin structure, e.g., a direction normal to a major surface to the substrate. Correspondingly, a vertical axis may be perpendicular to a main plane of extension or a main surface of the substrate or a coplanar surface of a layer formed thereon, such as the bottom layer or the top layer. Terms such as "above" and "under" as used herein may accordingly refer to opposite directions along the vertical axis, with respect to a reference. As herein, the term "horizontal" denotes a horizontal axis being perpendicular to the vertical axis. In embodiments where the device resulting from the method includes a substrate supporting the aforementioned layers forming the fin structure, a "vertical" direction/plane may be understood as a direction/plane being perpendicular to a main plane of extension or a main surface of the substrate. Correspondingly, a "horizontal" direction/plane may be understood as a direction parallel to a main plane of extension or a main surface of the substrate.

The terms "fin" or "fin-structure" as used herein may refer to a fin-shaped feature having a length and width extension in the horizontal direction and a height extension in the vertical direction. The width direction may also be referred to as a lateral direction of the fin. The fin-shaped features may be formed using standard fin-based processes, in which for example the stacked structure of the bottom layer and the top layer may be provided with trenches defining and separating the fins.

The term "nanopore" as used herein refers to an opening or channel extending in, and usually through, the fin. Generally, the nanopore extends at least through the semiconductor layer comprised in the fin. The prefix nano refers to the fact that a diameter, or width, or cross-sectional size of the pore may range from 1 to 100 nm. Generally, the width of the nanopore ranges from 1 to 34 nm, from 1 to 20 nm, usually ranging from 5 to 15 nm.

The disclosure will now be described by a detailed description of several embodiments of the disclosure. It is clear that other embodiments of the disclosure can be configured according to the knowledge of persons skilled in the art without departing from the technical teaching of the disclosure, the disclosure being limited only by the terms of the appended claims.

Figure 18:
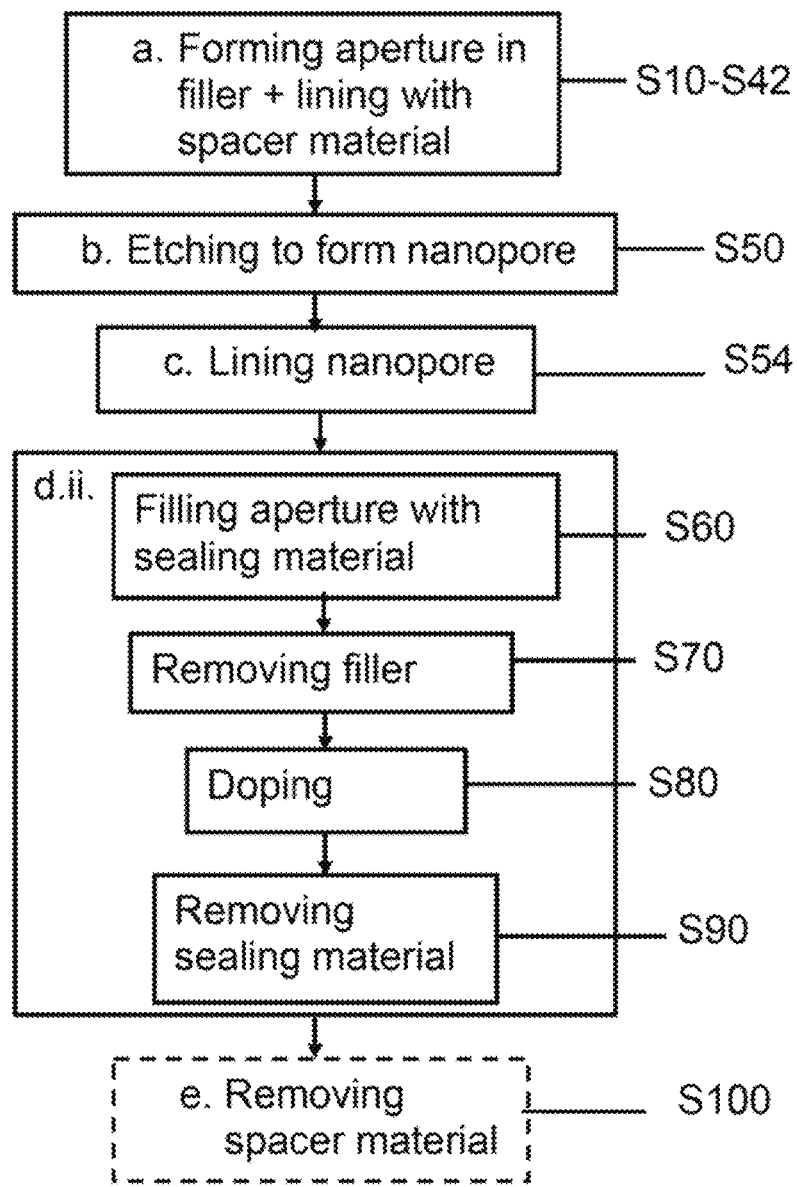
FIG. 18 is a flowchart showing the main steps of a method according to the first main embodiment of the present disclosure.
Figure 19:
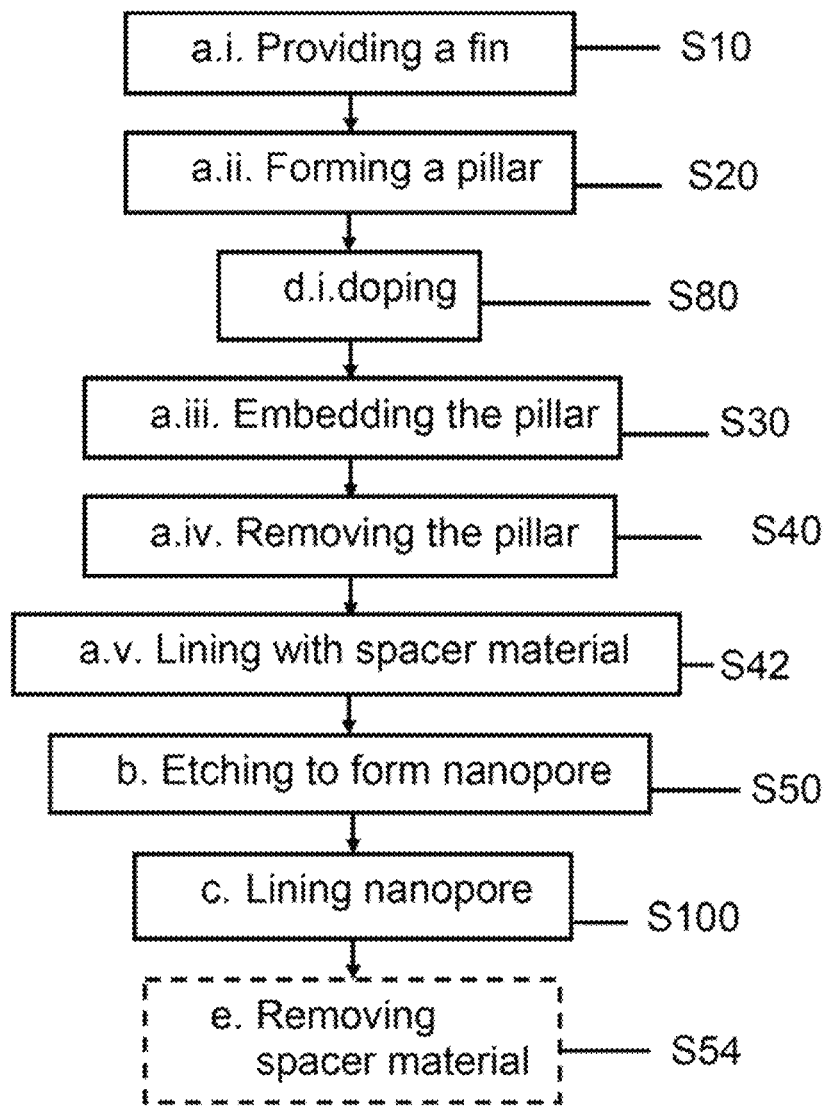
FIG. 19 is a flowchart showing the main steps of a method according to the second main embodiment of the present disclosure.

In a first aspect, the present disclosure relates to a method for forming a nanopore transistor for biosensing (1), comprising steps a, b, c, and d. FIGS. 18 and 19 depict two main embodiments of the method. We now refer to FIGS. 1 to 7 where intermediates formed during step a are depicted, and to FIG. 19 where the main steps involved in step a are represented in a flowchart. Step a comprises forming (S40) an aperture (140) in a filler material (130) by:

i. providing (S10, FIG. 1) a fin structure (100) comprising at least a bottom semiconductor layer (110) and a top layer (120);

ii. patterning (S20, FIGS. 2 and 3) the top layer (120) to form a pillar (122);

iii. laterally embedding (S30, FIGS. 4 and 5) the pillar (122) in a filler material (130);

iv. forming (S40, FIG. 6) an aperture (140) in the filler material (130) by removing the pillar (122); and v. lining (S42, FIG. 7) the aperture (140) with a spacer material (160), thereby reducing a size (e.g., the width) of the aperture (140).

Figure 8:
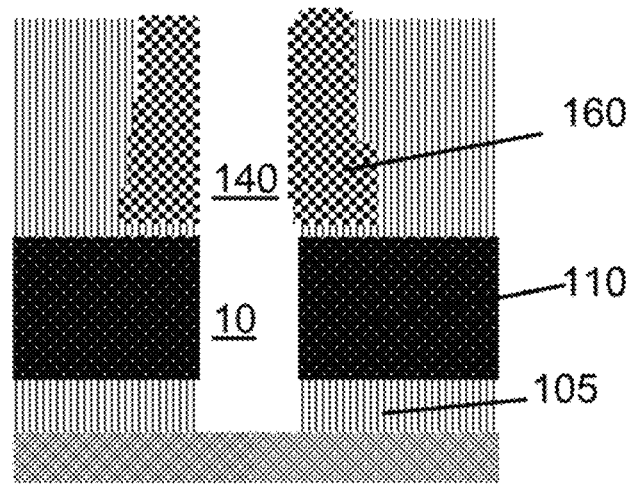

We now refer to FIG. 8 where an intermediate formed during step b is depicted. Step b of the method may performed after step a, usually directly after step a. It comprises forming (S50, FIG. 8) a nanopore (10) in the bottom semiconductor layer (110) by etching through the aperture (140).

Figure 9:
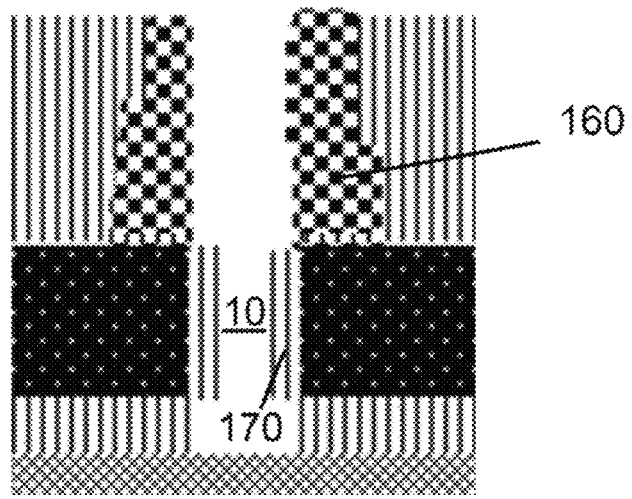

We now refer to FIG. 9 wherein an exemplary embodiment is depicted where the method further comprises a step c after step b, of lining (S54) the nanopore with a gate dielectric material (170), thereby forming a gate dielectric. By forming a gate dielectric, the size of the nanopore may be beneficially reduced. The gate dielectric material may generally be an oxide, generally silicon oxide, usually a silicon oxide obtained by thermal oxidation.

In embodiments, between step b and step c, a step b' of cleaning the inner sides of the nanopore may be performed to facilitate step c.

Figure 17:
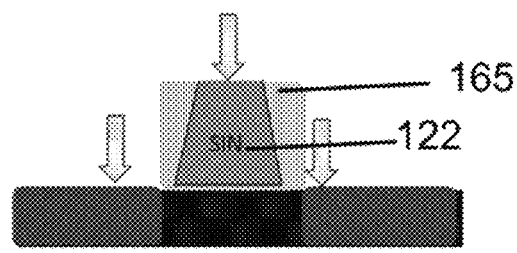
FIG. 17 is a schematic representation of a vertical cross-section through an exemplary intermediate structure during step d.i.

We now refer to FIGS. 10 to 13 where intermediates formed during step d in a first main embodiment are depicted, to FIG. 18 where the main steps involved in that embodiment are presented in a flowchart, to FIG. 17 where an intermediate formed during step d in a second main embodiment is depicted, and to FIG. 19 where the main steps involved in the second main embodiments are represented in a flowchart. Step d comprises forming (FIG. 13 or 17) a source (200) and a drain (210) by either:

i. Between steps a.ii and a.iii, doping (S80, FIG. 17) the bottom semiconductor layer (110) by ion implantation using the pillar (122) as a mask, or ii. After step b, filling (S60, FIGS. 10, 11) the aperture (140) with a sealing material (180) so that the sealing material (180) is coplanar with the filler material (130), thereby forming a post (190) comprising the sealing material (180) and the spacer material (180);

removing (S70, FIG. 12) the filler material (130) selectively with respect to the post (190), thereby exposing a part (111) of the bottom semiconductor layer (110);

doping (S80, FIG. 13) the bottom semiconductor layer (110) by ion implantation by using the post (190) as a mask; and removing (S90, FIG. 15) the sealing material (180).

In embodiments, a step a (S100, FIGS. 18 and 19) of removing the spacer material may be performed. In some embodiments, the spacer material and the sealing material are the same, and the steps (S90) of 1) removing the sealing material in in step d.ii and 2) removing the spacer material in step a may be performed simultaneously.

By employing a pillar structure formed of a top layer and a bottom layer, and cutting the top layer into a pillar structure, the pillar structure can be used as a sacrificial structure for forming an etch aperture that is self-aligned in the lateral direction of the fin.

In embodiments, the device resulting from the method may include a substrate supporting the afore-mentioned layers forming the fin structure. In such embodiments, the semiconductor fin of step a may be supported by a substrate. When the substrate is present, step b may comprise forming the nanopore also in the substrate.

In embodiments, the nanopore may have a width ranging from 1 to 34 nm, from 1 nm to 20 nm, usually ranging from 5 to 15 nm. These widths can be beneficial as they allow the sensing of biopolymers such as DNA and RNA strands. The nanopore is arranged in a channel region present between the drain region and the source region of the fin. The channel region becomes an actual channel as the sensed molecule passes through the opening. The distance D between the source and the drain regions corresponds to the length of the channel and may for instance range from 20 to 60 cm. The present method is, however, also applicable to longer and shorter channels.

In embodiments, the length extension of the nanopore may be oriented in the vertical direction, i.e., perpendicularly to the top surface of the bottom semiconductor layer.

In embodiments, a cross-section of the nanopore taken perpendicularly to the length extension thereof may be of any shape. Generally, the width of the cross-section measured in the plane of the top surface of the bottom semiconductor layer ranges within 20%, 10%, usually 5% of the length of the cross-section measured in said plane. Generally, the width and the length of the cross-section are the same, such as in the case of a square or circular cross-section.

The nanopore may, in one example, have a substantially uniform diameter, or cross section, along its length (measured perpendicularly to the top surface of the bottom semiconductor layer). However, other configurations are also possible. In an embodiment, the nanopore may have a tapered or funnel-shaped profile, e.g., a diameter that decreases towards the bottom or base of the fin. Such a gradually reduced opening size may allow for an improved control of the flow through the opening, usually such that only one sample strand at a time is guided through the opening. The tapered profile may, for example, be obtained by a wet etching process, such as potassium hydroxide (KOH) etching, resulting in a V-shaped profile along the (111) planes (in case of Si). Such a profile may comprise a facet arranged at an angle of 54.7° to the silicon surface. Other examples include reactive ion etching (RIE), which may be sequenced with sidewall passivation, using for example polymerization, to achieve the desired cross-sectional profile of the opening.

We now refer to FIG. 1 where an exemplary structure (100) resulting from step a.i is depicted. In embodiments, step a.i may comprise forming the fin structure by a lithography comprising a dry etching step. The fin structure (100) comprises a bottom semiconductor layer (110) and a top layer (120). The width of the fin may for instance range from 20 to 40 nm but the present method is applicable to wider or narrower fins. In embodiments, the fin structure has a bottom semiconductor layer (110) having a top surface having two longitudinal parallel sides separated by a width of from 20 to 40 nm. A reduced fin width, or a reduced cross-section of the fin, can be beneficial in that it may reduce the drive current during the operation of the device.

In embodiments, the nanopore may be centered with respect to the width so that the distances d1 and d2 between each longitudinal side (113, 114) and the nanopore are within 3 nm of one another, usually within 2 nm of one another.

In embodiments, the distances along the top surface of the bottom semiconductor layer between each longitudinal side and the nanopore may range from 5 to 15 nm, and are within 3 nm, usually within 2 nm of one another.

In embodiments, the ratio between the width of the nanopore (measured at the top surface of the bottom semiconductor layer) and the width (W) of the top surface of the bottom semiconductor layer of the fin may range from 0.12 to 0.85, from 0.30 to 0.85, from 0.50 to 0.85, usually from 0.60 to 0.85. A high ratio can be beneficial because it allows the use of a smaller fin width, which in turn reduces the drive current during the operation of the device.

In embodiments, the bottom semiconductor layer, of which the resulting fin may be formed, may for example be formed of silicon, such as the top silicon layer of a silicon on insulation (SOI) substrate.

In embodiments, the top layer may comprise a mask material. For instance, the mask material may be $Si_3N_4$.

In embodiments (not depicted), the top layer may comprise a first mask material and a second mask material, different from the first mask material, and arranged on top of the first mask material, wherein the first material is an etch stop material protecting the bottom layer during etching of the second mask material. This allows for a better process control of the top layer patterning, resulting in a reduced risk of etch-back of the bottom layer during the pillar formation. Hence, a method is obtained which is compatible with a bottom layer having a reduced thickness.

In embodiments, the first mask material may be formed of $SiO_2$, $Si_3N_4$, SiOC, and silicon oxynitride (SiON), and wherein the second mask material is selected from amorphous silicon (a-Si), TiN, $SiO_2$, $Si_3N_4$, SiOC, and silicon oxynitride (SiON). Generally, the first mask material and the second mask material are selected so as to achieve an etch selectivity between the mask layers, thereby enabling an etch stopping effect of the double mask. Such combinations may for example be a first mask material of $SiO_2$ combined with a second mask material of a-Si. This can be particularly beneficial when the bottom layer, forming the fin, is formed of Si, since the intermediate first mask material of $SiO_2$ allows for the pillar pattern to be transferred into the second mask material without damaging or etching back the underlying Si fin.

Figure 2:
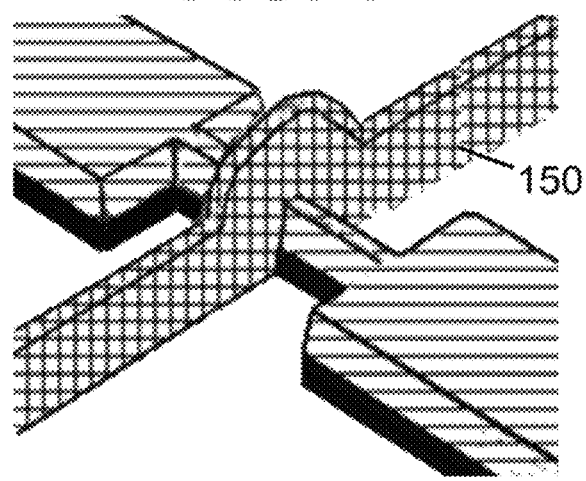
Figure 3:
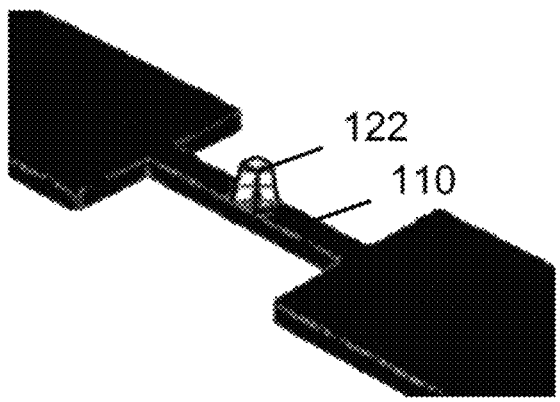
Figure 4:
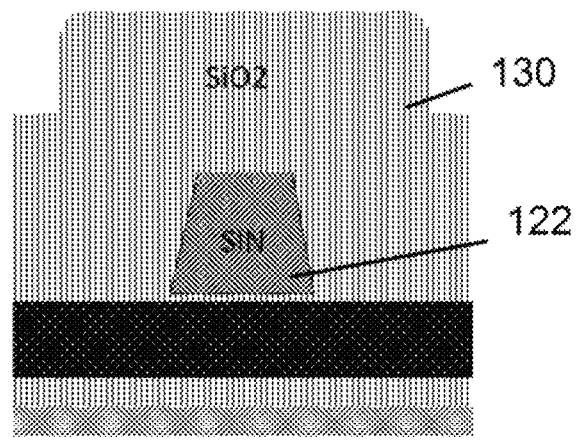
FIGS. 4 to 13 and 15 are schematic representations of vertical cross sections through intermediate structures formed in steps a.iii to a of an embodiment of the present disclosure.

We now refer to FIG. 3 where an exemplary structure resulting from step a.ii is depicted. This structure comprises a pillar (122) and may for instance be formed by self-aligning (S22) the pillar on the bottom layer using a line mask (150) intersecting the fin structure, as depicted in FIG. 2 for an exemplary embodiment. In other words, a line mask may be used to form the top layer of the fin structure into the pillar. The line mask may extend in a direction intersecting the length direction of the fin, such as, for example, orthogonal to the length direction of the fin, such that the region in which the line mask overlaps the material of the top layer defines the etch mask used when cutting the top layer into the pillar. The resulting pillar may thus be self-aligned in the lateral direction on the fin, whereas the lengthwise position may be determined by the lithographic process forming the line mask.

In embodiments, the line mask may have a width which is within 20%, 10%, 5%, usually 1% of the width of the fin structure it intersects. Generally, the width of the line mask is the same as the width of the fin structure it intersects. This can provide the benefit of forming a pillar that has equal lateral dimensions, thereby enabling the formation of a nanopore having equal lateral dimensions (e.g., having a square or circular cross-section).

To form the pillar (122), the top layer (120) may be etched selectively with respect to the bottom semiconductor layer. In the case of a bottom Si layer and a top $Si_3N_4$ layer, this step can be performed by a suitable ion etching technique.

After the line mask is removed, the resulting structure is a fin having the top layer present only at the intersections of the two lithography patterns, thereby forming a pillar. The height of the resulting pillar may be equal to the thickness of the top layer and typically ranges from the thickness of the semiconductor layer (110) and three time the thickness of the semiconductor layer (110), while one of its two lateral dimensions equals the width of the nanowire while the other of its two lateral dimensions equals the width of the line mask.

Figure 5:
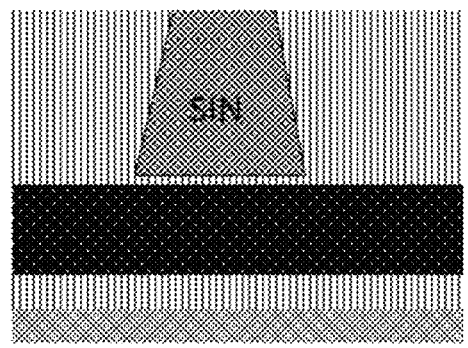

We now refer to FIG. 5 where an exemplary structure resulting from step a.iii. is depicted. In embodiments, the filler material (130) may be selected such that an etch selectivity to the pillar material is achieved. The filler material may for example be $SiO_2$ or $Si_3N_4$. Generally, the filler material is $SiO_2$.

Step a.iii may comprise a first sub-step (see FIG. 4) of embedding the pillar in the filler material in such a way that all the pillar surfaces are covered, followed by a second sub-step (see FIG. 5) of removing a top portion of the filler material so as to expose the top surface of the pillar. In embodiments, the first sub-step may result in a thickness of filler material equal to at least 150% of the height of the pillar. The second sub-step can, for example, be performed by chemical mechanical planarization. In the resulting structure, the top surface of the pillar and the top surface of the filler are co-planar.

Figure 6:
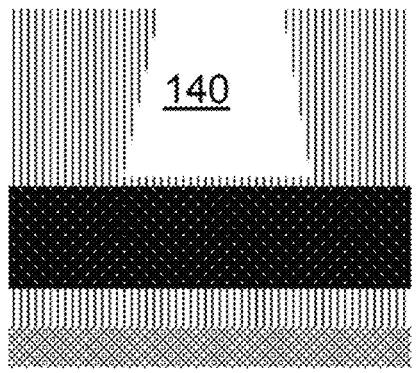

We now refer to FIG. 6 where an exemplary structure resulting from step a.iv. is depicted. Removing the pillar can, for instance, be performed by etching the pillar selectively with respect to the filler.

Figure 7:
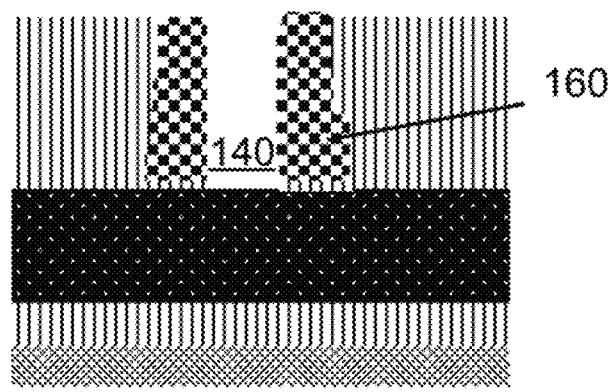

We now refer to FIG. 7 where an exemplary structure resulting from step a.v is depicted.

Step a.v of lining the aperture (140) with a spacer material (160) can reduce a size of the aperture.

The spacer material may, for example, be provided in an atomic layer deposition (ALD) process or by oxidation (e.g., thermal or anodic) of the sidewalls of the aperture. Oxidation can have the benefit of enabling the size of the opening to be monitored during the oxidation process. Adding the spacer material can allow for the size of the resulting nanopore to be reduced to a desired size, such as down to a width as small as 1 nm. The spacer material may, for example, be silicon dioxide ($SiO_2$), silicon nitride ($Si_3N_4$), silicon oxycarbide (SiOC), or a metal such as titanium nitride (TiN), tantalum nitride (TaN) or aluminum nitride (AlN). Generally, the filler material (130) is silicon dioxide.

Figure 10:
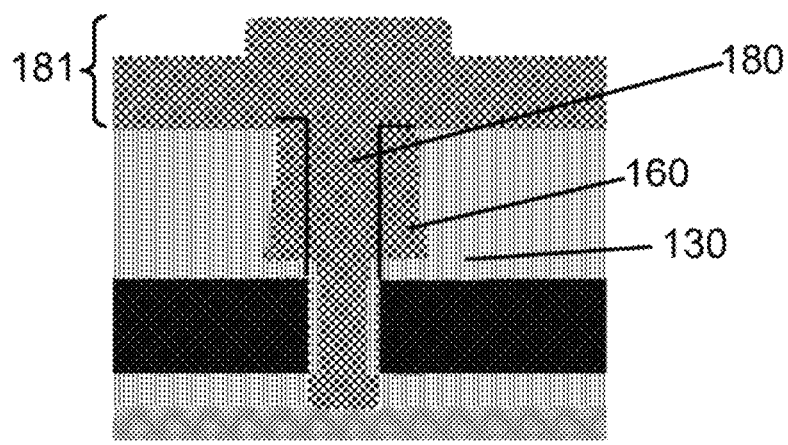

We now refer to FIG. 10 where an exemplary embodiment is depicted, wherein the step (S60) of filling the aperture during step d.ii comprises overfilling the aperture (140) with a sealing material (180) so that the sealing material (180) covers part of the filler material (130).

In embodiments, the sealing material may be $Si_3N_4$.

Figure 11:
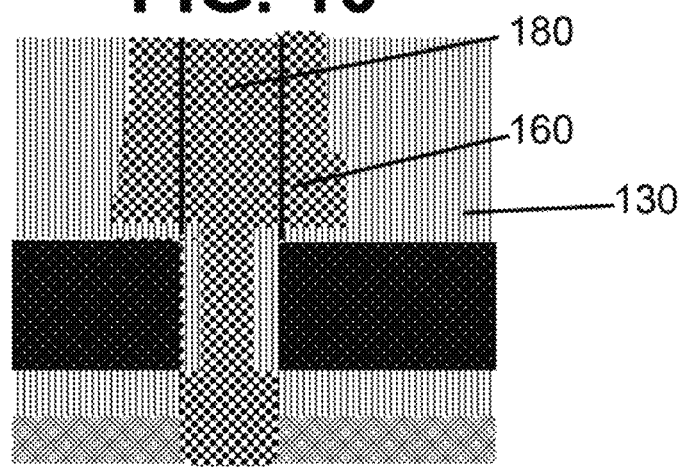

We now refer to FIG. 11 wherein overfilling the aperture is followed by removing a top portion (181) of the sealing material (180) until it no longer covers any filler material.

In embodiments, removing the top portion may be performed by a wet etch, a chemical mechanical planarization, or a combination of both.

Figure 12:
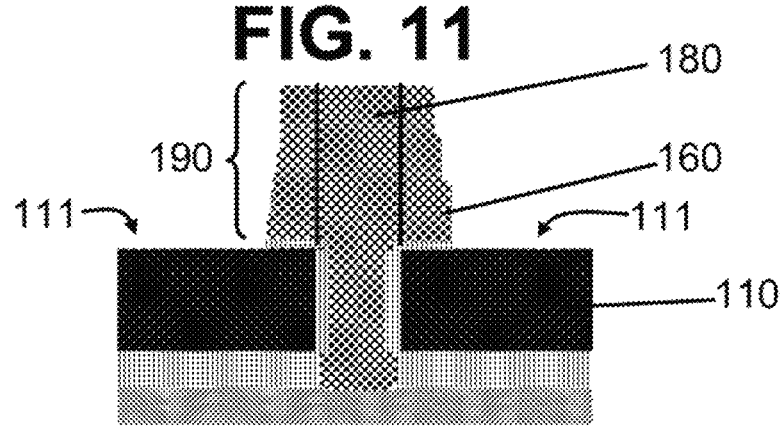

We now refer to FIG. 12 where the step (S70) of removing the filler material in step d.ii is depicted for an exemplary embodiment of the present disclosure. The resulting structure has the bottom semiconductor layer exposed around the post.

Figure 13:
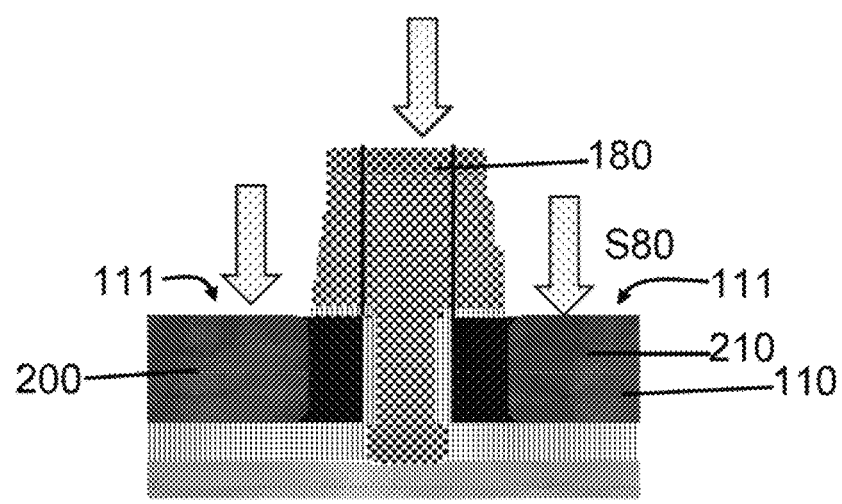

We now refer to FIG. 13 where the doping step (S80) in step d.ii is depicted for an exemplary embodiment of the present disclosure. In embodiments, the ion implantation in the bottom semiconductor layer may form a source and a drain separated by 20 to 60 nm. In embodiments, the nanopore may be centered with respect to the source and the drain so that the distance, along the top surface of the bottom semiconductor layer, between the nanopore and the source is within 3 nm, usually within 2 nm, of the distance along the top surface between the nanopore and the drain. In embodiments, the distance along the top surface of the bottom semiconductor layer between the nanopore and the source and between the nanopore and the drain ranges from 5 to 25 nm and these distances are within 3 nm, usually 2 nm of one another.

Figure 14:
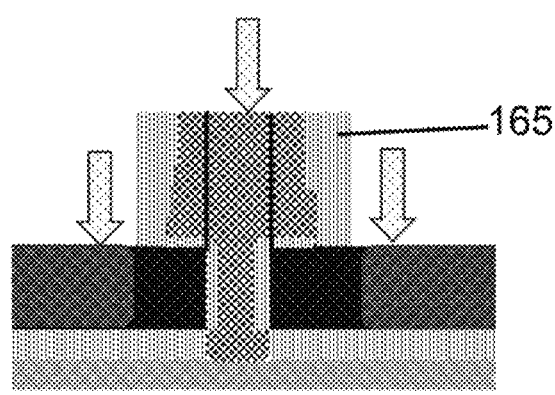
FIG. 14 is a schematic representation of a vertical cross-section through an exemplary intermediate structure during step d in an embodiment further comprising a step c', after a step (S70) of removing the filler material and before a doping step, of forming spacers around the post, and wherein step c.ii.c comprises using the post and the spacers as a mask.

We now refer to FIG. 14 depicting the result of an embodiment of the method further comprising a step c', after the step (S70) of removing the filler material and before the doping step (S80), of forming spacers around the post, wherein the doping step (S80) comprises using the post and the spacers as a mask. This can be beneficial when implantation is desired farther from the nanopore or when a multi-implant scheme is desired as is sometimes the case in CMOS technologies.

In embodiments, the method may further comprise a step d', after step d, of exposing the bottom semiconductor layer to heat so as to activate dopants introduced in step d.

Figure 15:
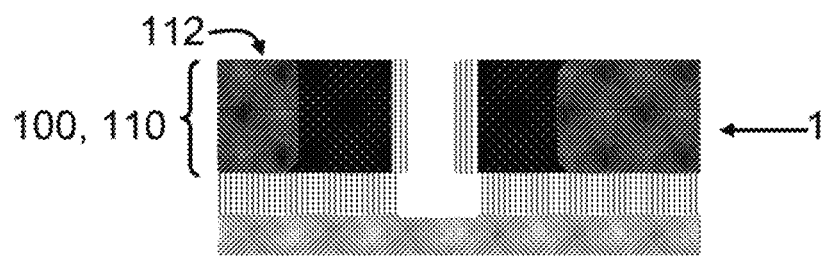
Figure 16:
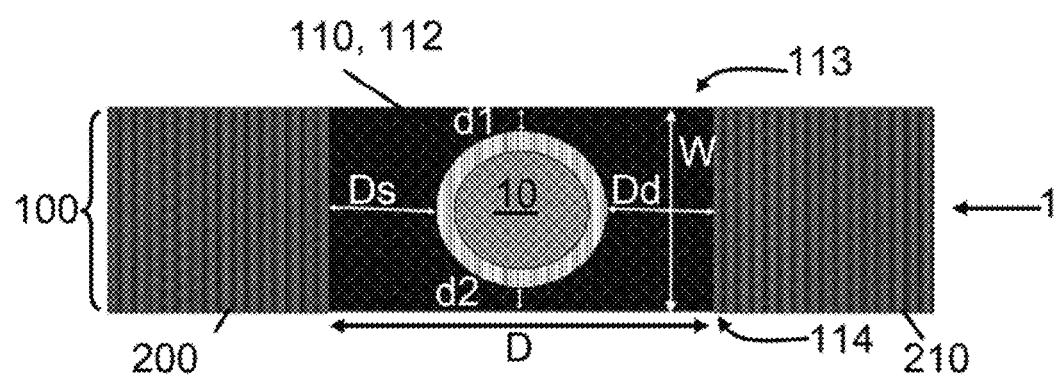
FIG. 16 is a schematic representation of a top view of FIG. 15.

In embodiments, steps (S80) of removing the sealing material and step e. may be performed together by simultaneously exposing the sealing material and the spacer material to a same etching liquid. The resulting structure is depicted in FIGS. 15 and 16 which includes a nanopore (10) which is self-aligned with respect to the channel width W, the source (200), and the drain (210) of the transistor (1).

We now refer to FIG. 17 which depicts an exemplary embodiment wherein step d is performed between step a.ii and step a.iii. In the example of FIG. 17, a dielectric spacer, e.g., $SiO_2$, is formed around the post.

We now refer to FIG. 8 which depicts an exemplary embodiment wherein step b is performed by etching through the bottom silicon layer (110), and if present through the first mask material (105) (which is the case in FIG. 8), by using an etchant capable to etch the bottom silicon layer (and if present the first mask material) selectively with respect to the filler material. The etching method used may, for example, be reactive ion etching.

In embodiments, step b may be performed after step a and before step d.ii and the sealing material may be the same as the spacer material. For example, both the sealing material and the spacer material may be silicon nitride.

In a second aspect, the present disclosure relates to a nanopore transistor for biosensing, formed by a method according to any one of the preceding claims. We now refer to FIGS. 15 and 16.

In embodiments, the nanopore transistor for biosensing (1) may comprise a fin structure (100) comprising a semiconductor layer (110) having:

i. a top surface (112) having two longitudinal parallel sides (113, 114) separated by a width W ranging from 20 to 40 nm, ii. a nanopore (10) piercing the semiconductor layer (110), and lined with a gate material (170), and iii. ion implantation in the semiconductor layer (110) forming a source (200) and a drain (210) separated by a distance D ranging from 20 to 60 nm, wherein the nanopore (10) is centered with respect to the width W so that the distances d1 and d2 between each longitudinal side and the nanopore are within 3 nm of one another, wherein the nanopore (10) is centered with respect to the source (200) and the drain (210) so that the distance Ds along the top surface between the nanopore (10) and the source (200) is within 3 nm of the distance Dd along the top surface between the nanopore (10) and the drain (210).

Such a nanopore transistor, with such precision in the placement of the nanopore, is believed not have been made before the present disclosure. Such a device can be produced with high consistency in the nanopore placement precision and devices of high sensitivity can be obtained showing a high signal to noise ratio.

In embodiments, the width of the nanopore measured in the plane of the top surface may range from 1 to 34 nm, from 1 nm to 20 nm, usually ranging from 5 to 15 nm.

In embodiments, the distances along the top surface between each longitudinal side and the nanopore may be within 2 nm of one another.

In embodiments, the distances along the top surface between each longitudinal side and the nanopore may range from 5 to 15 nm and are within 3 nm, usually within 2 nm of one another.

In embodiments, the distance along the top surface between the nanopore and the source may be within 2 nm of the distance along the top surface between the nanopore and the drain.

In embodiments, the distance Ds along the top surface between the nanopore and the source and the distance Dd between the nanopore and the drain ranges from 5 to 25 nm and these distances may be within 3 nm, usually 2 nm of one another.

In embodiments, the ratio between the width of the nanopore (measured in the plane of the top surface of the fin and along the width of the fin) and the width (W) of the top surface of the fin may range from 0.12 to 0.85, from 0.30 to 0.85, or from 0.50 to 0.85, usually ranging from 0.60 to 0.85. A high ratio can be beneficial because it allows the use of a smaller fin width, which in turn reduces the drive current during the operation of the device.

Any feature of the second aspect may be as correspondingly described in the first aspect.

It is to be understood that although various embodiments, specific constructions, and configurations, as well as materials, have been discussed herein for devices according to the present disclosure, various changes or modifications in form and detail may be made without departing from the scope and spirit of this disclosure. For example, any formulas given above are merely representative of procedures that may be used. Functionality may be added or deleted from the block diagrams and operations may be interchanged among functional blocks. Steps may be added or deleted to methods described within the scope of the present disclosure.

The invention claimed is:

1. A method for forming a nanopore transistor for biosensing, the method comprising:
   (a) forming an aperture in a filler material by:
      (i) providing a fin structure comprising at least a bottom semiconductor layer and a top layer;
      (ii) patterning the top layer to form a pillar;
      (iii) laterally embedding the pillar in the filler material;
      (iv) forming the aperture in the filler material by removing the pillar;
      (v) lining the aperture with a spacer material, thereby reducing a size of the aperture;
   (b) forming a nanopore in the bottom semiconductor layer by etching through the aperture;
   (c) lining the nanopore with a gate dielectric material, thereby forming a gate dielectric; and
   (d) forming a source and a drain by either:
      (i) between steps a.ii and a.iii, doping the bottom semiconductor layer by ion implantation using the pillar as a mask, or
      (ii) after step b,
         filling the aperture with a sealing material so that the sealing material is coplanar with the filler material, thereby forming a post comprising the sealing material and the spacer material;
         removing the filler material selectively with respect to the post, thereby exposing a part of the bottom semiconductor layer;
         doping the bottom semiconductor layer by ion implantation by using the post as a mask; and
         removing the sealing material.

2. The method of claim 1, wherein the step a.ii comprises self-aligning the pillar on the bottom semiconductor layer using a line mask intersecting the fin structure.

3. The method of claim 1, wherein the filler material is silicon dioxide.

4. The method of claim 1, wherein the spacer material is selected from the group consisting of: silicon dioxide; silicon nitride, silicon oxycarbide, and a metal.

5. The method of claim 1, wherein the bottom semiconductor layer comprises silicon.

6. The method of claim 1, wherein the top layer comprises a first mask material and a second mask material, different from the first mask material, and arranged on top of the first mask material, wherein the first mask material is an etch stop material protecting the bottom semiconductor layer during etching of the second mask material.

7. The method of claim 6, wherein the first mask material is selected from the group consisting of: silicon dioxide, silicon nitride, silicon oxycarbide, and silicon oxynitride, and wherein the second mask material is selected from the group consisting of: amorphous silicon, titanium nitride, silicon dioxide, silicon nitride, silicon oxycarbide, and silicon oxynitride.

8. The method of claim 1, wherein the gate dielectric material is an oxide.

9. The method of claim 1, further comprising a step c' performed:
   between steps a.ii and d if step d.i is performed, comprising forming spacers around the pillar, and comprising using the pillar and the spacers as a mask during step d.i, or
   during step d.ii, between the step of removing the filler material and the doping step, comprising forming spacers around the post, and comprising using the post and the spacers as a mask during the doping step.

10. The method of claim 1, wherein step b is performed after step a.v and before step d and wherein the sealing material is the same as the spacer material.

11. The method according to claim 10, wherein both the sealing material and the spacer material is silicon nitride.

12. The method of claim 1, wherein in step d.ii, the step of filling the aperture with the sealing material comprises overfilling the aperture with the sealing material so that the sealing material covers part of the filler material, followed by removing a top portion of the sealing material until it no longer covers the filler material.

13. The method of claim 1, further comprising a step d', after step d, of exposing the bottom semiconductor layer to heat so as to activate dopants introduced in step d.

14. The method of claim 1, wherein a width of the nanopore ranges from 1 to 34 nm.

15. The method of claim 1, wherein a width of the nanopore region ranges from 1 to 20 nm.

16. The method of claim 1, wherein a width of the nanopore region ranges from 5 to 15 nm.

* * * * *